United States Patent [19]
Tower

[11] Patent Number: 5,161,773
[45] Date of Patent: Nov. 10, 1992

[54] METHOD AND APPARATUS FOR CONTROLLING FLUID FLOW

[75] Inventor: Allen J. Tower, North Lawrence, N.Y.

[73] Assignee: Numed, Inc., Hopkinton, N.Y.

[21] Appl. No.: 561,671

[22] Filed: Aug. 1, 1990

[51] Int. Cl.⁵ .............................................. F16K 7/07
[52] U.S. Cl. ....................................... 251/5; 604/167
[58] Field of Search ................... 251/5; 604/158, 163, 604/165, 167

[56] References Cited

U.S. PATENT DOCUMENTS

| | | | |
|---|---|---|---|
| 3,039,733 | 6/1962 | Mattioli | 251/5 |
| 3,717,174 | 2/1973 | Dewall | 251/5 X |
| 4,256,130 | 3/1981 | Smith et al. | 251/5 X |
| 4,700,694 | 10/1987 | Shishido | 604/158 X |
| 4,813,938 | 3/1989 | Raulerson | 604/167 |
| 4,932,959 | 6/1990 | Horzewski et al. | 604/165 X |

FOREIGN PATENT DOCUMENTS 2160390  6/1973  Fed. Rep. of Germany .......... 251/5

Primary Examiner—John C. Fox
Attorney, Agent, or Firm—Wall and Roehrig

[57] ABSTRACT

A combination valve and clamping device is provided in which a flexible elastic inner lining is secured in a tubular outer shell having a port for introducing a fluid therebetween. A source of pressure such as a hypodermic syringe is used to cause the inner elastic sleeve to collapse and deform internally upon itself to surround and form a seal about a catheter located therein, positioning it within the shell. Alternatively, if nothing is present in the shell, the sleeve is collapsed on itself to prevent leakage of a fluid through the valve mechanism.

8 Claims, 2 Drawing Sheets

METHOD AND APPARATUS FOR CONTROLLING FLUID FLOW

BACKGROUND OF THE INVENTION

This invention relates to a method and apparatus for controlling the flow of a fluid through a conduit and the positioning of an element in a conduit. More particularly, this invention pertains to an elastic valve apparatus for preventing leakage of blood through an introducing sheath inserted in a vessel and around a catheter inserted in the sheath.

PRIOR ART

In the treatment of certain medical conditions, it is frequently necessary to repeatedly introduce a catheter for injection of fluids into blood vessels of a patient. It is common practice in order to minimize discomfort to the patient and to insure repeated access to the blood vessel in question, to install an "introducing sheath" in a more or less permanent fashion at an appropriate site on a patient. The sheaths are then used as the conduit through which a catheter can be introduced for injection of the desired medication or treatment materials into the blood vessel of the patient. Frequently, in treatment of cancers and other types of serious illnesses, repeated insertions of a catheter are required to introduce a variety of medications and this requires insertion and removal of a catheter repeatedly over time. While the catheter ferrule can be tightened about the introducing sheath ferrule to form a tight seal during the use of the catheter, when the catheter is being inserted and withdrawn and after the catheter is withdrawn, blood or other fluids can readily exit through the introducing sheath around the catheter and directly out after the catheter is removed. This causes an undesired leakage of blood or other fluid, both during and after insertion of the catheter.

Various methods have been suggested in the past for limiting this leakage with the most successful method known to applicant being the use of a latex diaphragm mounted in the introducing sleeve which has a small hole in the center and through which the catheter can be inserted. As the catheter is inserted, the diaphragm expands to accommodate the catheter and reduces the leakage of blood or other fluids about the catheter during use in the introducing sheath. When the catheter is withdrawn, the diaphragm closes to shut off the flow of fluids. While this has worked in certain instances, particularly where the catheter is of a very small diameter, for larger sized catheters and larger sized introducing sheaths, the latex diaphragm has tended to leak excessively. Also, in certain types of treatments, it has been found that a balloon catheter has been required and it has been found to be virtually impossible to insert a latex balloon catheter through a latex diaphragm, since the diaphragm tends to strip the latex balloon from the catheter. Accordingly, when a latex balloon catheter is to be used, the introducing sheath has generally had to be one without any leakage prevention means.

OBJECTS AND SUMMARY OF THE INVENTION

It is therefore an object of the present invention to provide a method and apparatus for overcoming the limitations of the prior art.

It is another object of the present invention to provide a method and apparatus for sealing around a catheter inserted in an introducing sheath.

It is a further object of the present invention to provide a method and apparatus for sealing around a catheter inserted into an introducing sheath and to shut off the flow of fluid through the sheath after removal of the catheter.

It is yet another object of the present invention to provide an elastic valve for closing off the flow of fluids through a conduit.

It is yet a further object of the present invention to provide an elastic valve which may be repeatedly closed and opened to control flow of a fluid through a tube.

It is a still further object of the present invention to provide an elastic valve for shutting off a conduit that can be securely closed about an object in the fluid flow path in the conduit.

It has also been found to be very desirable in various medical procedures to be able to temporarily shut off the flow of blood or other fluids without damaging the blood vessel, the introducing sheath, the catheter, or without having to install a cap or other seal.

In a preferred embodiment of the present invention, this is accomplished by providing a valve having a generally cylindrical rigid outer shell with a fluid port in the side wall thereof and an inner flexible elastic tubular lining forming an inner shell sealed together at their ends to form a fluid-tight chamber therebetween, together with a syringe for introducing air into said chamber so as to collapse the elastic lining of the tube onto itself to shut off the flow of fluid through the tube. With this embodiment, if a catheter is in place in the tube, the valve will shut off leakage or fluid flow through the tube by sealing about the catheter.

BRIEF DESCRIPTION OF THE DRAWING

Further objects of the invention, together with additional features and advantages accruing therefrom will be apparent from the following description of a preferred embodiment shown in the accompanying drawings in which.

DETAILED DESCRIPTION OF THE PREFERRED EMBODIMENT

Figure 1:
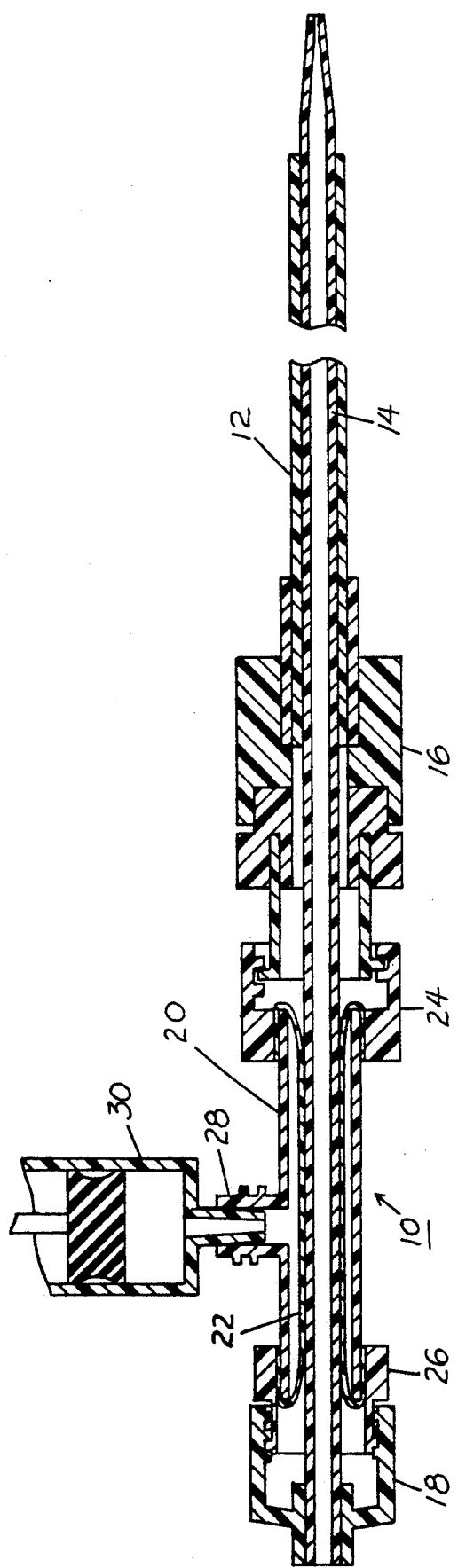
FIG. 1 is a cross sectional view of a valve in accordance with the present invention attached to an introducing sheath and catheter.

Referring now to FIG. 1, there is shown a valve 10 installed on an introducing sheath 12 through which a catheter 14 has been inserted, as might be used in a patient for introducing a treatment or medication. The introducing sheath 12 is usually a plastic tube long enough to be semi-permanently placed in a patient's blood vessel, as is well known in the art. The usual ferrule 16 is provided at the proximal end for reception of catheter ferrules, closure ferrules, and other well-known devices used with a semi-permanently installed introducing sheath. The catheter 14 has a ferrule 18 which engages with the ferrule 16 on the introducing sheath with one ferrule being male, and the other ferrule being female. As shown in FIG. 1, the valve 10 of the present invention has a corresponding female 24 and male 26 connector at the ends thereof for installation in series in this sequence.

In the prior art, the catheter 14 would be introduced into the sheath 12 and the ferrule 18 locked about the ferrule 16. In this position, leakage of blood or other fluids around the catheter and out through the ferrules would be prevented as long as the two ferrules were locked together in sealing relationship. On removal of the catheter 14, a cap or other closure would have to be applied to the ferrule 16 to prevent leakage of fluids through the sheath 12. Also, during installation of the catheter, which can take some time, and during the removal of the catheter, there can be, and frequently is, significant leakage around the catheter through the sheath.

In the prior art the ferrule 16 has sometimes been provided with a latex diaphragm at one end which has been essentially a layer of latex rubber having a small hole in the center which is adapted to expand and contract as a catheter 14 is inserted into and withdrawn from the diaphragm. As explained above, this has worked for smaller sizes somewhat, but has always left some leakage, and for larger sizes, has not been particularly satisfactory. Also, the diaphragm prevents usage of a catheter with a balloon on the end, as is frequently used in treatment of certain types of medical conditions.

Accordingly, applicant has provided the valve 10 in accordance with the present invention which is installed on the end of the introducing sheath 12 and which acts as a shut off for blood or other fluids leaking from the sheath, and yet permits easy introduction of a catheter 14 into the sheath while simultaneously providing a sealing function around the catheter as it is installed, used and as it is withdrawn.

Figure 2:
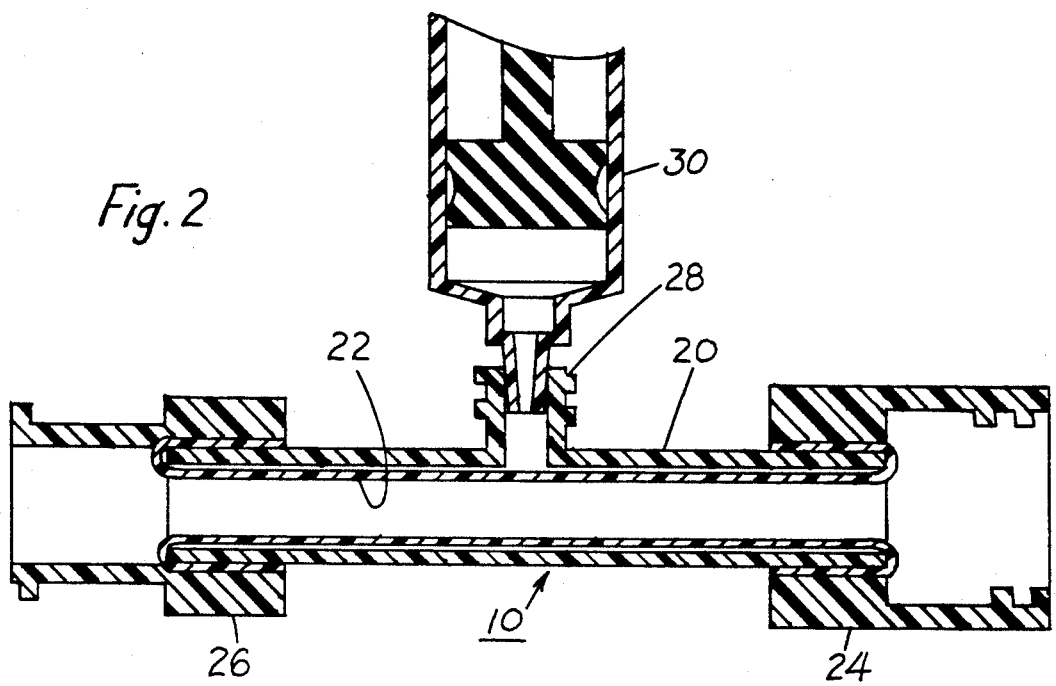
FIG. 2 is a cross sectional view of the valve of the present invention.

Referring now to FIG. 2, the valve 10 of the present invention comprises an outer tubular body member 20 which is generally made of a polyurethane or other rigid or semi-rigid material that can be easily sterilized. The length of outer body 20 depends on the size of the internal diameter necessary to accommodate different size catheters for various treatment regimens. The valve body 20 can be sized so as to permit easy passage of a balloon catheter therethrough without damaging the balloon. The body 20 is lined with a flexible tubular lining 22 which is generally formed of a thin layer of high strength polyethylene or other suitable elastic material so as to completely line the interior of the valve body 20. The tubular sleeve 22 generally is longer than the body 20 and the ends are folded back about the outer ends of the body 20 and cemented about the ends of the body to form an air-tight seal about the circumference of the ends of the body 20. Suitable ferrules 24 and 26 are then sealed about the ends of the body 20 and the turned back sleeve 22 to secure the whole assembly to a form that can be easily and readily connected to other ferrules such as the ferrule 16 of the introducing sheath 12 of FIG. 1.

The provision of the inner tubular lining 22 completely sealed about both ends of the body 20 forms a compartment between the inner sleeve and outer body portion. The inner elastic sleeve 22 may be elastically deformed, as will be described in detail. The port 28 is shown as a tapered fitting for introducing of a standard hypodermic syringe for introducing air or other fluid into the compartment between the inner sleeve and outer body of the valve 10. As shown in FIG. 2, a standard hypodermic syringe 30 is provided to introduce a sterile saline solution, for instance, through the port 28 into the space between the outer body 20 and the inner sleeve 22.

Figure 3:
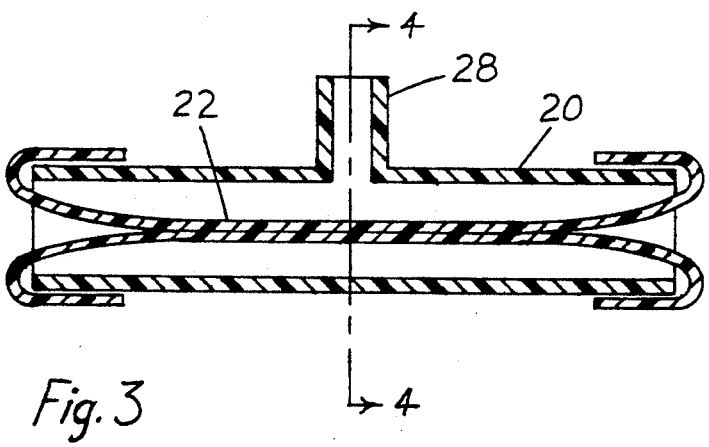
FIG. 3 is a cross sectional view of the valve of FIG. 2 in the actuated condition without a catheter present.
Figure 4:
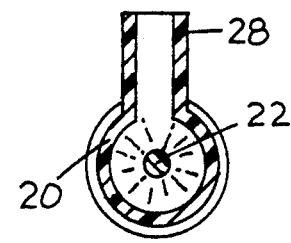
FIG. 4 is a cross sectional view taken along line 4—4 of FIG. 3.

Referring now to FIG. 3, it will be seen that as air or other fluid is introduced into the space between the outer body 20 and the sleeve 22, the elastic sleeve 22 will be inwardly deformed and collapsed upon itself until it forms a solid mass at the center of the circular body 20, throughout approximately half the length of the body 20, totally closing off and sealing the valve body against fluid flow from one end to the other. The valve, as shown in FIGS. 3 and 4 is totally closed off and prohibits flow of blood or other fluids therethrough. As may be seen in FIG. 4, the center of the assembly becomes a solid mass of high strength polyethylene which, together with the remaining part of the thin tubular film, forms a complete seal at each end of the tube against any flow of fluid. If the valve 10 of FIG. 1 were actuated to the condition shown in FIG. 3, no fluid could flow through the sheath 12 in either direction.

When it is desired to permit flow of fluid through the valve 10, the hypodermic syringe 30 can be retracted to reduce the pressure and to allow the elastic sleeve 22 to return to its normal position, as shown in FIG. 2. In this configuration free flow of fluid is permitted through the valve body 20. When the tubular lining 22 has returned to its normal relaxed position of FIG. 2, a catheter having a balloon on the end thereof may be readily and easily inserted through the valve body and into the introducing sheath for insertion into the patient for the necessary treatment regimen. Alternatively, of course, the deformation of the sleeve 22 may be used to restrict but not totally shut off the flow of fluid through the valve body so that fluid flow may be regulated as well as stopped.

Figure 5:
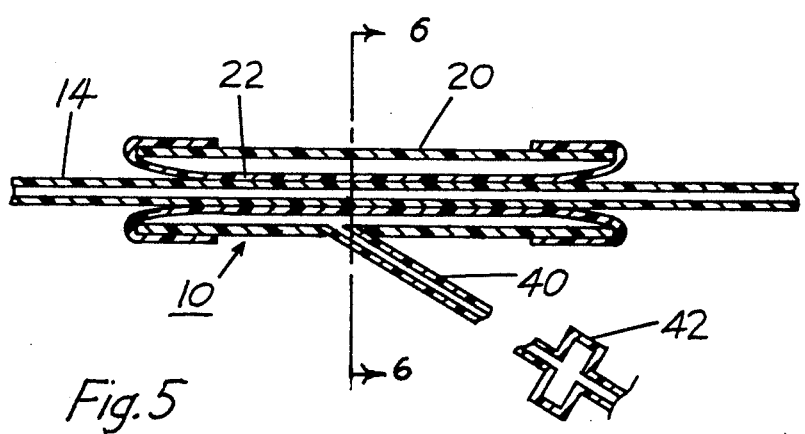
FIG. 5 is a view similar to FIG. 3 of another embodiment of the present invention with the valve actuated to seal around a catheter inserted therethrough.
Figure 6:
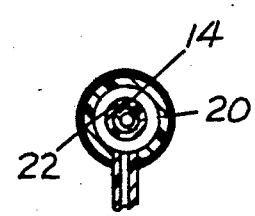
FIG. 6 is a cross sectional view taken along line 6—6 of FIG. 5.

Referring now to FIG. 5, the valve 10 is shown with a catheter 14 inserted therethrough. With the valve actuated as shown in FIG. 6, a seal is formed around the circumference of the catheter to prevent any leakage of blood or other fluids past the catheter and out of the introducing sheath.

By limiting the amount of pressure applied by the hypodermic syringe 30 to the tubular lining 22 of the valve 10, a sealing action may be provided around the circumference of the catheter, while still allowing it to be inserted and withdrawn from the introducing sheath, without leakage. Once the catheter is in place, if desired, the pressure applied by the hypodermic syringe may be increased sufficiently to physically hold the catheter in place by causing a sufficient length of the flexible lining 22 to grip and surround the catheter so that no other clamping mechanism is required to hold the catheter in place during use. Since the clamping pressure is applied over an extended area, there is no danger of collapsing the catheter. The catheter is thus held in place and leakage is totally sealed off thereabout during use without the necessity of a locking ferrule or other sealing device.

The flexible inner lining of the valve body 20 is generally made of a high strength polyethylene material which has a very strong non-permeable characteristic and yet can be repeatedly flexed to a very considerable degree without bursting or fatigue which might cause leakage. Wall thickness of 2/1,000 of an inch and thinner will provide the required flexibility and strength. In a preferred embodiment of the present invention, a tubular sleeve having a wall thickness of approximately 5/10,000 of an inch has been found satisfactory. It will thus be seen that the inner sheath 22 causes virtually no restriction of the interior of the valve body 20 in the unactivated position and thus offers an easy and simple way of inserting a complicated catheter such as a balloon catheter without causing any damage to the catheter going through the valve mechanism. This high strength polyethylene tube also is extremely elastic and can be readily collapsed about the catheter to totally seal off fluid flow through the inserting sheath about the catheter and also when no catheter is present, to totally seal off the valve body itself against fluid flow. It will be recognized that the amount of sealing can be adjusted by varying the pressure or amount of fluid used to cause the deformation of the sleeve 22 into the interior of the tubular body 20. As indicated above, this fluid pressure can be increased sufficiently to physically hold a catheter in place or other wire or instrument that may be placed in the valve body so that the valve body can be used not only to prevent fluid flow, but it also can be used to clamp and position instruments relative to the valve body.

By adjusting the length of the valve body and the tubular elastic sleeve relative to its diameter and the strength of any object to be clamped within it, surface pressures can be regulated so as not to collapse the catheter or other device placed within the valve 10. In at least one prior art device known to applicant, when it was attempted to clamp an outer sleeve about the inner catheter, the device actually collapsed the catheter as well as the sleeve so that the catheter could no longer be used for the introduction of medication into the patient. Applicant's valve can be adjusted to prevent leakage about an instrument wire, catheter, temperature sensor, or other apparatus inserted through the introducing sheath, as well as to completely shut off the introducing sheath against leakage of blood or other fluids.

While I have shown a typical hypodermic syringe as the device for applying pressure to the valve 10, it should be understood that other means of applying pressure or introducing fluid for collapsing the flexible inner lining 22 onto itself can be used. Also, it should be obvious that whatever means is used, some type of ratchet mechanism or other means for holding the pressure can advantageously be used to maintain the desired sealing pressure for extended periods of time.

As shown in FIG. 5, the valve body 20' may have molded as an integral part thereof a hollow tube 40 shown entering the outer body 20' at an angle of approximately 30° which tube has on its end a usual ferrule 42 or other mechanism for introducing the sealing and clamping fluid pressure. The body 20' can be molded with the tube 40 integral therewith for certain applications. When the valve 10, as shown in FIG. 5 is actuated about a catheter positioned therein, it will cause the flexible lining 22 to tightly wrap around and collapse upon the catheter 14 to form a seal about the outer surface of the catheter, while allowing fluid to flow through the catheter for the treatment of the patient (FIG. 6).

As shown in FIGS. 3 and 5, the extent of collapse of the flexible lining 22 onto itself or about the catheter can be varied from a very small amount to 50-75% of the length of the valve body 20 depending upon the amount of pressure applied to the cavity between the inner and outer sleeves of the body. By varying the wall thickness of the flexible sleeve 22 and the length and diameter of the body 20, various footprint pressures can be obtained for sealing about fragile or very strong catheters or other devices inserted through the valve body for a wide variety of applications of this flow control and positioning device.

The valve of the present invention can be used in a wide variety of applications as well as a shut off valve for preventing leakage of blood or other fluids from an inserting sheath. It can be used to temporarily shut off the flow of blood in bypass vein or artery applications; it can also be used to position instruments in a catheter or other tubular inserting sheath; and it can also be used to prevent leakage around fragile or delicate catheters as well as providing sealing around specialized catheters having balloons or other devices on the end thereof. In the later application, the sleeve is totally unpressurized to allow free passage of the tip of the catheter carrying the specialized instrumentation and then it is suitably inflated to collapse about and seal off leakage of fluids about the catheter during the rest of its insertion into proper operating position and during its use and withdrawal.

A unique fluid controlling device having a wide variety of applications has thus been provided for effectively controlling the flow of fluids through a conduit and for positioning a device within a conduit while simultaneously preventing leakage around the device within the conduit.

While this invention has been explained with reference to the structure disclosed herein, it is not confined to the details as set forth and this application is intended to cover any modifications and changes as may come within the scope of the following claims.

What is claimed is:

1. A combination sealing/positioning device for use on an introducer sheath for balloon dilation catheters in which leakage during insertion and withdrawal is eliminated and a selected position maintained which comprises:

an outer body member mounted on one end of the introducer sheath and having an internal diameter at least as large as that of the introducer sheath;

a thin tubular film of elastic material forming an interior lining of said outer body member with the ends thereof sealed about the ends of said outer body member to form a fluid receiving chamber therebetween;

means for introducing a fluid into said fluid receiving chamber for selectively collapsing said elastic material lining upon a balloon dilation catheter therein and/or itself;

said thin film elastic material in the relaxed condition adhering intimately with the interior diameter of said body member to permit unimpeded full diameter access to said introducer sheath;

so that a balloon dilation catheter can be introduced through said sealing/positioning device into said introducer sheath without damage to the balloon and fluid flow can be sealed off while said dilation catheter is being installed or withdrawn through said introducer sheath.

2. A device in accordance with claim 1 wherein said outer body member is a short plastic tube having a port at the center thereof and said thin film of elastic material is a sleeve of high strength polyethylene film sealed about the periphery of the ends of the plastic tube.

3. A device in accordance with claim 2 wherein said fluid introducing means comprises a syringe connected to the port in said plastic tube so that air may be injected between said plastic tube and sleeve to collapse said sleeve upon itself within said plastic tube to shut off flow through said tube.

4. A device in accordance with claim 2 wherein said polyethylene film has a thickness of 0.0005 inches.

5. A sealing/positioning device according to claim 1 wherein the length and diameter of said outer body member and elastic material lining are chosen to apply to a dilation catheter mounted therein an area of contact sufficient to seal off fluid flow thereabout upon introducing a first amount of fluid into said fluid receiving chamber; and to hold said dilation catheter fixed in position upon introducing a second amount of fluid into said fluid receiving chamber without damaging said dilation catheter.

6. The method of inserting a balloon dilation catheter through an insertion sheath which comprises:
forming a tubular outer body member adapted to receive therein the compressible object;
forming a thin film elastic tubular lining inside said tubular outer body;
sealing said tubular lining at each end to said tubular outer body member to form a fluid receiving chamber therebetween;
mounting said body member on an introducer sheath;
passing a dilation catheter through said body member and lining when said lining is in intimate contact with the inside of said body member;
injecting a quantity of fluid at a first pressure into said fluid receiving chamber to cause said lining to form a fluid seal about said dilation catheter;
passing said dilation catheter through said fluid seal formed by said lining until the dilation balloon is in the desired position within a body vessel;
increasing the pressure on the quantity of fluid injected into said fluid receiving chamber to fix said balloon dilation catheter in position in said body member during actuation of said balloon;
decreasing the pressure on the quantity of fluid injected into said fluid receiving chamber to sealing level;
withdrawing said dilation catheter from said introducer sheath and body member without leaking fluid; and
increasing said pressure to close off the interior of said body member upon removal of said dilation catheter.

7. A combination sealing/positioning device for use on an introducer sheath for catheter treatment devices in which leakage during insertion and withdrawal is eliminated and a selected position maintained which comprises:
an outer body member mounted on one end of the introducer sheath and having an internal diameter at least as large as that of the introducer sheath;
a thin tubular film of elastic material forming an interior lining of said outer body member with the ends thereof sealed about the ends of said outer body member to form a fluid receiving chamber therebetween;
means for introducing a fluid into said fluid receiving chamber for selectively collapsing said elastic material lining upon a treatment device positioned therein and/or itself;
said thin film elastic material in the retracted condition adhering intimately with the interior diameter of said body member to permit unimpeded full diameter access to said introducer sheath;
so that a treatment device can be introduced through said sealing/positioning device and said introducer sheath without damage to said device and fluid flow can be sealed off while said device is being installed or withdrawn through said introducer sheath.

8. The method of inserting a catheter treatment device through an introducer sheath which comprises:
forming a tubular outer body member adapted to receive therein the treatment device;
forming a thin film elastic tubular lining inside said tubular outer body;
sealing said tubular lining at each end to said tubular outer body member to form a fluid receiving chamber therebetween;
mounting said body member on an introducer sheath;
passing a treatment device through said body member and lining when said lining is in intimate contact with the inside of said body member;
injecting a quantity of fluid at a first pressure into said fluid receiving chamber to cause said lining to form a fluid seal about said treatment device;
passing said treatment device through said fluid seal formed by said lining until the treatment device is in the desired position within a body vessel;
increasing the pressure on the quantity of fluid injected into said fluid receiving chamber to fix said treatment device in position in said body member during actuation of said device;
decreasing the pressure on the quantity of fluid injected into said fluid receiving chamber to sealing level;
withdrawing said treatment device from said introducer sheath and body member without leaking fluid; and
increasing said pressure to close off the interior of said body member upon removal of said treatment device.

* * * * *